US010813856B2

(12) United States Patent
Tampieri et al.

(10) Patent No.: US 10,813,856 B2
(45) Date of Patent: Oct. 27, 2020

(54) PHYSICAL SOLAR FILTER CONSISTING OF SUBSTITUTED HYDROXYAPATITE IN AN ORGANIC MATRIX

(71) Applicant: CONSIGLIO NAZIONALE DELLE RICERCHE, Rome (IT)

(72) Inventors: Anna Tampieri, Faenza (IT); Monica Sandri, Faenza (IT); Simone Sprio, Bologna (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 16/082,991

(22) PCT Filed: Mar. 6, 2017

(86) PCT No.: PCT/IB2017/051290
§ 371 (c)(1),
(2) Date: Sep. 7, 2018

(87) PCT Pub. No.: WO2017/153888
PCT Pub. Date: Sep. 14, 2017

(65) Prior Publication Data
US 2019/0070079 A1 Mar. 7, 2019

(30) Foreign Application Priority Data

Mar. 7, 2016 (IT) .................. 102016000023614

(51) Int. Cl.
*A61K 8/24* (2006.01)
*A61K 8/29* (2006.01)
*A61Q 17/04* (2006.01)
*A61K 8/19* (2006.01)
*C01B 25/32* (2006.01)
*A61K 8/02* (2006.01)
*A61K 8/65* (2006.01)
*A61K 8/73* (2006.01)
*A61K 8/85* (2006.01)
*A61K 8/86* (2006.01)

(52) U.S. Cl.
CPC .............. *A61K 8/24* (2013.01); *A61K 8/0283* (2013.01); *A61K 8/19* (2013.01); *A61K 8/29* (2013.01); *A61K 8/65* (2013.01); *A61K 8/733* (2013.01); *A61K 8/736* (2013.01); *A61K 8/85* (2013.01); *A61K 8/86* (2013.01); *A61Q 17/04* (2013.01); *C01B 25/322* (2013.01); *A61K 2800/412* (2013.01); *A61K 2800/413* (2013.01); *A61K 2800/84* (2013.01)

(58) Field of Classification Search
None
See application file for complete search history.

(56) References Cited

U.S. PATENT DOCUMENTS

2009/0074645 A1    3/2009  Hsi-Chin et al.
2015/0190320 A1*   7/2015  Tachon .................. A61K 8/29
                                                 424/401

FOREIGN PATENT DOCUMENTS

JP    2009155249 A  *  7/2009
WO   2010/109400 A2    9/2010
WO   2016/001871 A1    1/2016

OTHER PUBLICATIONS

JP2009155249A Machine Translation from Google Patents, accessed Dec. 7, 2019 (Year: 2009).*
Burnett & Wang, "Current Sunscreen Controversies: A Critical Review," Photodermatology, Photoimmunology & Photomedicine 27:58-67 (2011).
Ma et al., "Ecotoxicity of Manufactured ZnO Nanoparticles—A Review," Environmental Pollution 172:76-85 (2013).
Wu et al., "Toxicity and Penetration of TiO2 Nanoparticles in Hairless Mice and Porcine Skin After Subchronic Dermal Exposure," Toxicology Letters 191:1-8 (2009).
International Search Report and Written Opinion for corresponding Application No. PCT/IB2017/051290 (dated Jul. 28, 2017).
De Araujo et al., "Effect of Zn2+, Fe3+ and Cr3+ Addition to Hydroxyapatite for its Application as an Active Constituent of Sunscreens," J. Phys. Cont Series 249(1): 1-6 (2010).

* cited by examiner

*Primary Examiner* — Melissa L Fisher
(74) *Attorney, Agent, or Firm* — Troutman Pepper Hamilton Sanders LLP (Rochester)

(57) ABSTRACT

The present invention relates to a composition for the protection against solar radiation, consisting of an organic matrix, preferably a gelatin, and hydroxyapatite nanoparticles modified by the substitution of part of the phosphorus with titanium, and part of the calcium with iron.

3 Claims, 6 Drawing Sheets

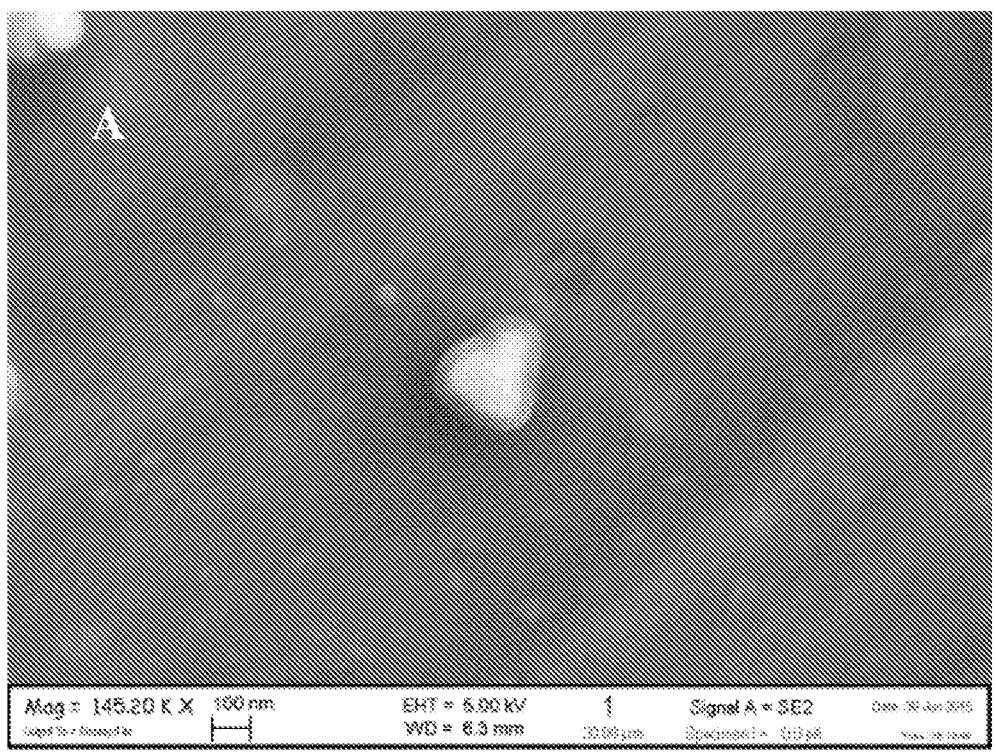
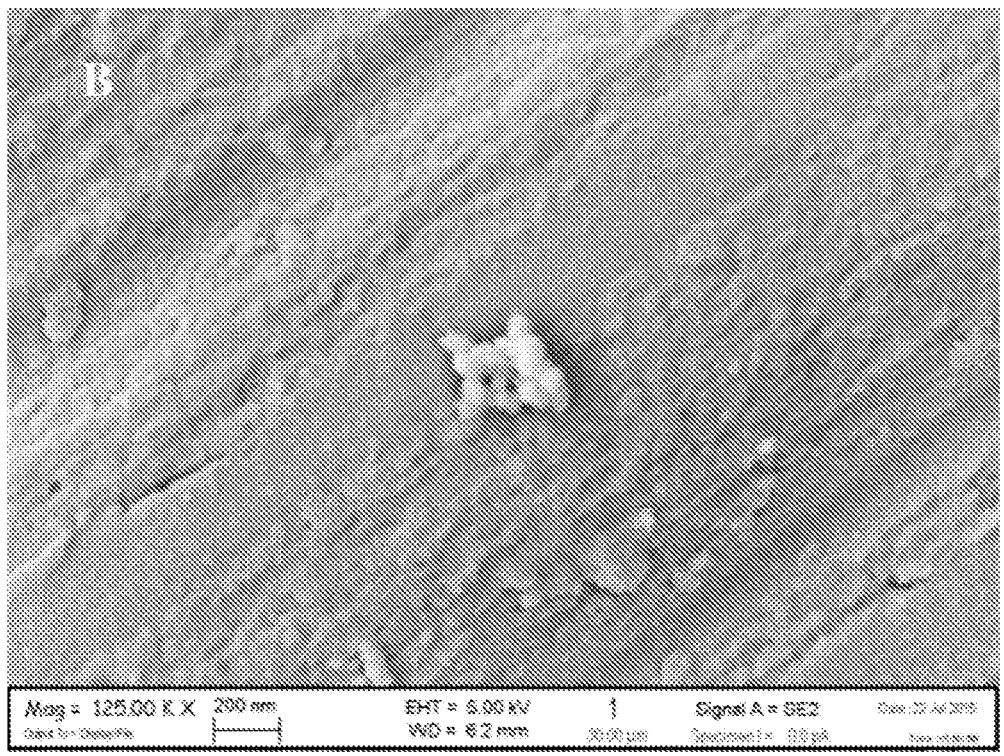
Fig. 1 to be continued

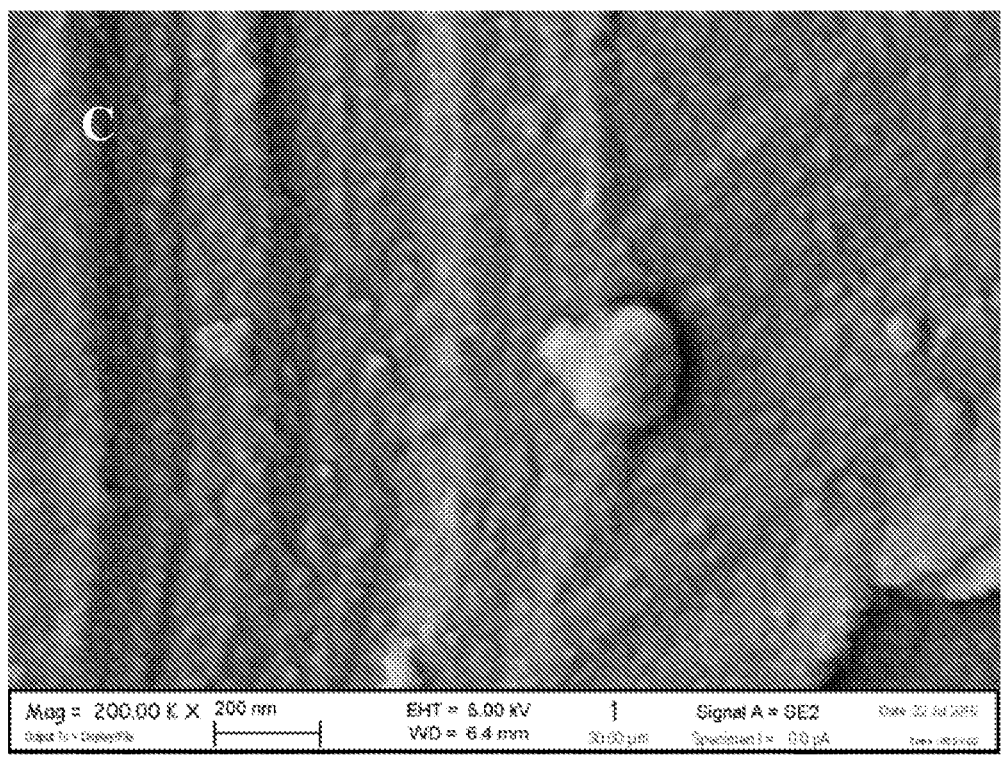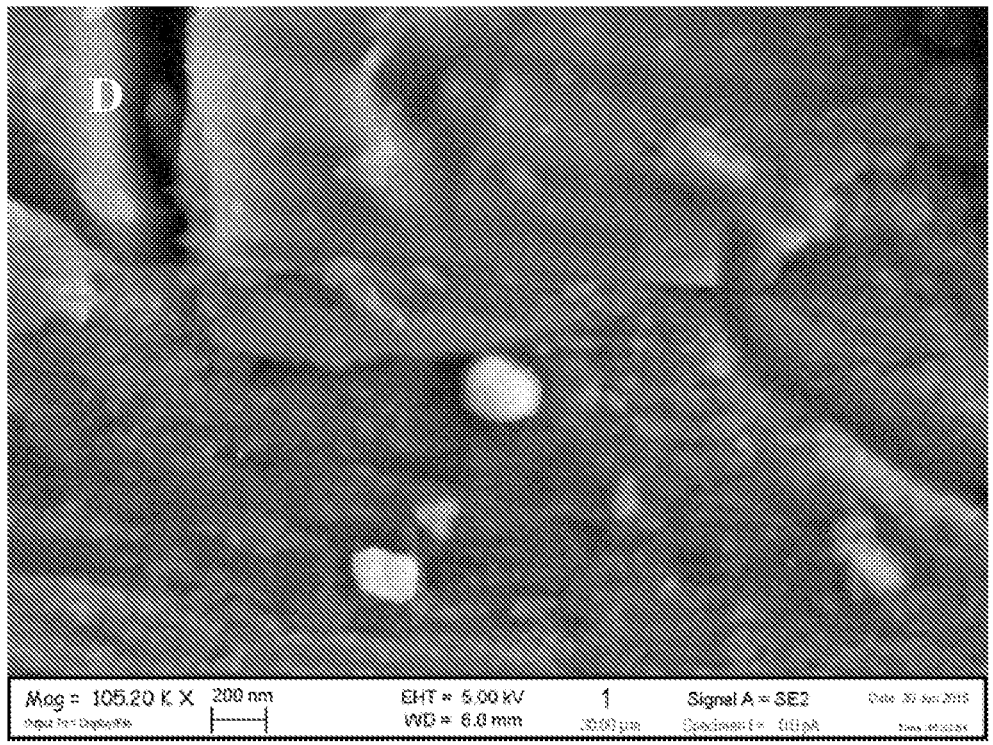
Fig. 1 to be continued

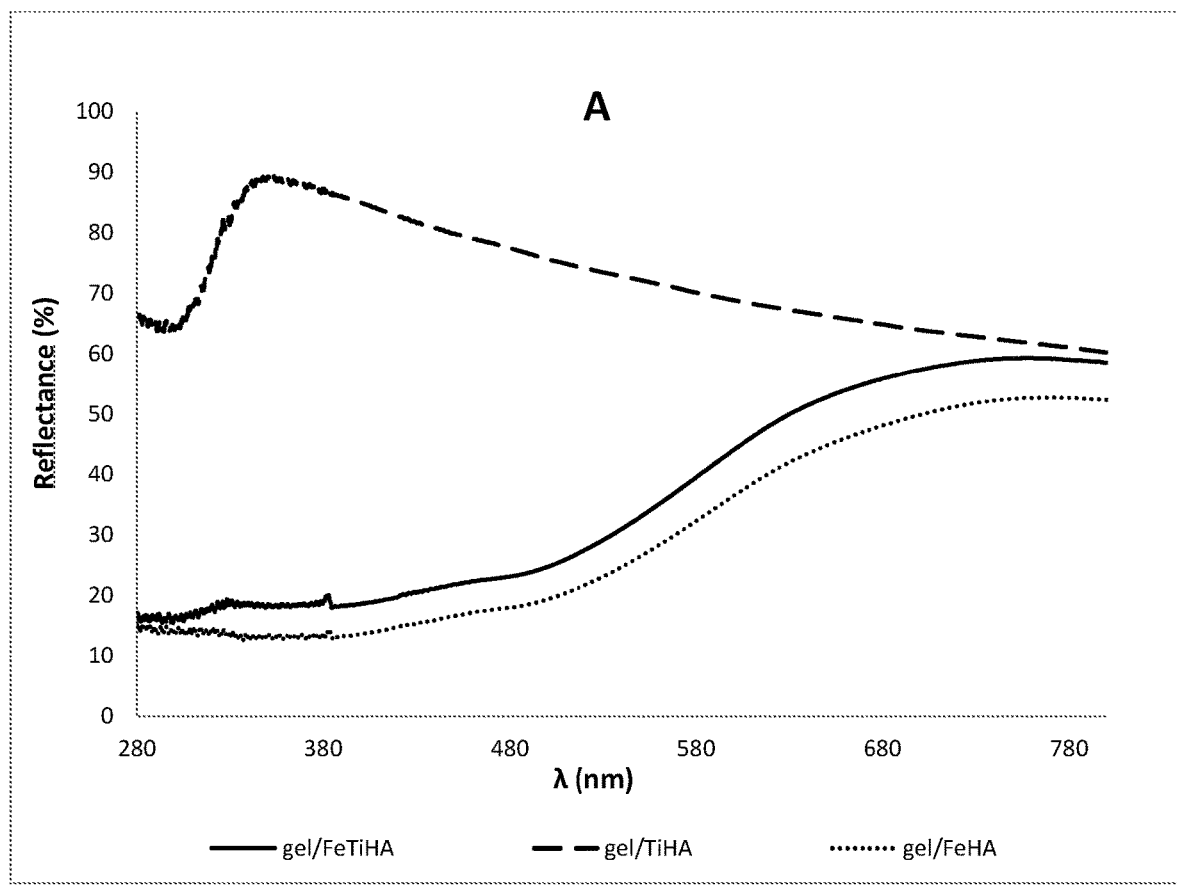
Fig. 3 to be continued

PHYSICAL SOLAR FILTER CONSISTING OF SUBSTITUTED HYDROXYAPATITE IN AN ORGANIC MATRIX

This application is a national stage application under 35 U.S.C. § 371 of PCT Application No. PCT/IB2017/051290, filed 6 Mar. 2017, which claims priority of Italy Application No. 102016000023614, filed 7 Mar. 2016, which are hereby incorporated by reference in their entirety.

FIELD OF THE INVENTION

The present invention relates to a physical solar filter, formed by particles of hydroxyapatite substituted with titanium and/or iron ions in an organic matrix consisting of a biocompatible polymer.

PRIOR ART

It is known that solar radiations, especially the ultraviolet (UV) component of the spectrum of these radiations, are responsible for photochemical degradation of various types. These can include fading and aging of paints, fabrics and plastic coatings, but above all alterations of the skin tissues in humans, potentially up to the onset of skin cancer; acute and chronic exposure to UV rays can in fact lead to sunburn, photoaging, photoimmunosuppression and a photocarcinogenity, which are of great concern for young people and in particular children.

UV radiation comprises the portion of the spectrum of wavelengths between 100 and 400 nm, which are further divided into UVC (100-290 nm), UVB (290-320 nm) and UVA (320-400 nm). UVC radiation exposure is of little practical interest, as wavelengths below 290 nm are absorbed by the ozone layer and do not reach the Earth's surface, while exposure to UVA and UVB is considered unavoidable.

In order to prevent or mitigate the negative effects of UV ray exposure, the so-called solar filters can be used, which are fluid compositions that can be spread on the part to be protected and which contain components able to reduce the amount of UV radiation that reaches the same part; due to this feature, solar filters are also commonly referred to as sunscreens. Although, as mentioned, UV exposure can cause degradation in manufactured articles and industrial products, in the remainder of the description reference will be made to the applications for skin protection, given the importance of the latter; it is anyway understood that the solar filters described herein can also be applied in other fields.

Solar filters can be divided into two main classes: a) chemical or biological filters, wherein the active components in photoprotection are organic molecules capable of absorbing UV rays; and b) physical or inorganic UV filters, comprising physical barriers that reflect radiation. Among the chemical photoprotection components, the one that is more widely used is the compound 1-(4-methoxyphenyl)-3-(4-tert-butylphenyl)-propane-1,3-dione, commonly referred to by the names of use methoxydibenzoylmethane butyl or avobenzone, while among the compounds with physical activity in particular $TiO_2$ and ZnO can be mentioned.

However, the solar filters currently on the market are not exempt from critical issues; the points discussed in relation to their use are related to their components and the effects of their distribution in the environment, as well as their degradation upon exposure to sunlight and the effect of the degradation products. For example, there are investigated the effects on the skin (e.g. irritation and sensitization) and the skin penetration of the cream components; the estrogenic effects of chemical UV filters; the photocatalytic activity and photodegradation through UV radiation exposure; and vitamin D deficiency caused by overuse of sunscreens, resulting in insufficient absorption of UV radiation by the skin.

The photocatalytic activity (third point mentioned above) is an undesired feature of any solar protection, since it might lead to the generation of free radicals and other reactive species that can themselves be the cause of some of the health problems associated with exposure to UV rays; in this regard, see for example the article "Current Sunscreen Controversies: A Critical Review" M. E. Burnett et al., Photodermatology *Photoimmunology and Photomedicine,* 2011, 27(6): 58-67.

This drawback is associated not only to chemical UV filters, for example containing the compound avobenzone as active ingredient, which are known to undergo photodegradation, but especially to the use of physical UV filters containing nanoparticles of $TiO_2$, $SiO_2$, $Fe_xO_y$, $Mg_xO_y$, ZnO. It was found that the use of these compounds in the form of nanoparticles improves the effectiveness thereof, resulting in a greater photoprotection effect, while causing however possible safety concerns related to the photocatalytic properties of these minerals under UV-visible light and their well-documented ability to generate reactive free radicals by UV radiation exposure. In addition, due to the increasing use of physical sunscreens, increasing concentrations of nanoparticles of $TiO_2$ and ZnO have been recently detected in the environment, especially in coastal waters. ZnO nanoparticles have ecotoxicological effects both in aquatic and terrestrial species within a wide range of taxa, and above certain levels of concentration in natural environments they may cause a significant risk for the environmental biota; see, for example, the article "Ecotoxicity of manufactured ZnO nanoparticles—A review" H. Ma et al., *Environmental Pollution,* 2013, 172, 76-85.

$TiO_2$ nanoparticles seem to show lower levels of toxicity on marine phytoplankton compared to ZnO, although they were found to have an ecotoxic effect on algae and *Daphnia*.

Another problem related to the use of UV filters based on inorganic nanoparticles relates to the epidermal penetration of the latter following the topical application of sunscreen. The stratum corneum is proved to be an effective barrier to prevent the entry of ZnO and $TiO_2$ nanoparticles in the deeper layers of the healthy skin, but a higher degree of penetration is observed in the case of damaged or diseased skin. In addition, some studies showed that micronized forms of titanium dioxide and zinc oxide (which, by reducing the size of the particles to the order of magnitude of nanometers, allow screening low-wavelength radiations such as UV but not visible light) used to prevent any undesired whitening effect in sunscreens, can result in increased penetration of the physical filter in the innermost layers of the epidermis, where it can trigger oxidative stress reactions resulting in depletion of collagen, photoaging and a photocarcinogenity; in this regard, see for example the article "Toxicity and penetration of $TiO_2$ nanoparticles in airless mice and porcine skin after subchronic dermal exposure", Jianhong Wu et al., Toxicology letters 191 (2009) 1-8.

The main concerns caused by the use of $TiO_2$ and ZnO nanoparticles in physical UV filters are therefore related to their potential phototoxicity and their penetration, resulting in systemic and bioaccumulation effects in humans and other organisms.

The need to have active components for sunscreens that are free from the drawbacks outlined above, or in any case exhibit them to a lesser extent with respect to the materials currently used, is therefore still felt in the field.

The object of the present invention is to provide a photoactive material for use in solar filters with reduced phototoxicity and skin penetration features.

SUMMARY OF THE INVENTION

This object is achieved with the present invention which, in a first aspect thereof, relates to a composition comprising an organic matrix formed by polymer molecules, onto which are linked nanoparticles of hydroxyapatite substituted with titanium and/or iron ions, in which phosphorus is partially replaced by titanium in an amount between 8 and 50% atomic with respect to phosphorus, and/or in which calcium is partially replaced by iron in an amount between 2 and 40% atomic with respect to calcium, and wherein the amount of the organic matrix is between 5 and 60% by weight and the amount of substituted hydroxyapatite is between 35 and 90% by weight, the remaining part being constituted by water.

In a second aspect thereof, the invention relates to the process for obtaining said composition.

DETAILED DESCRIPTION OF THE INVENTION

Figure 1:
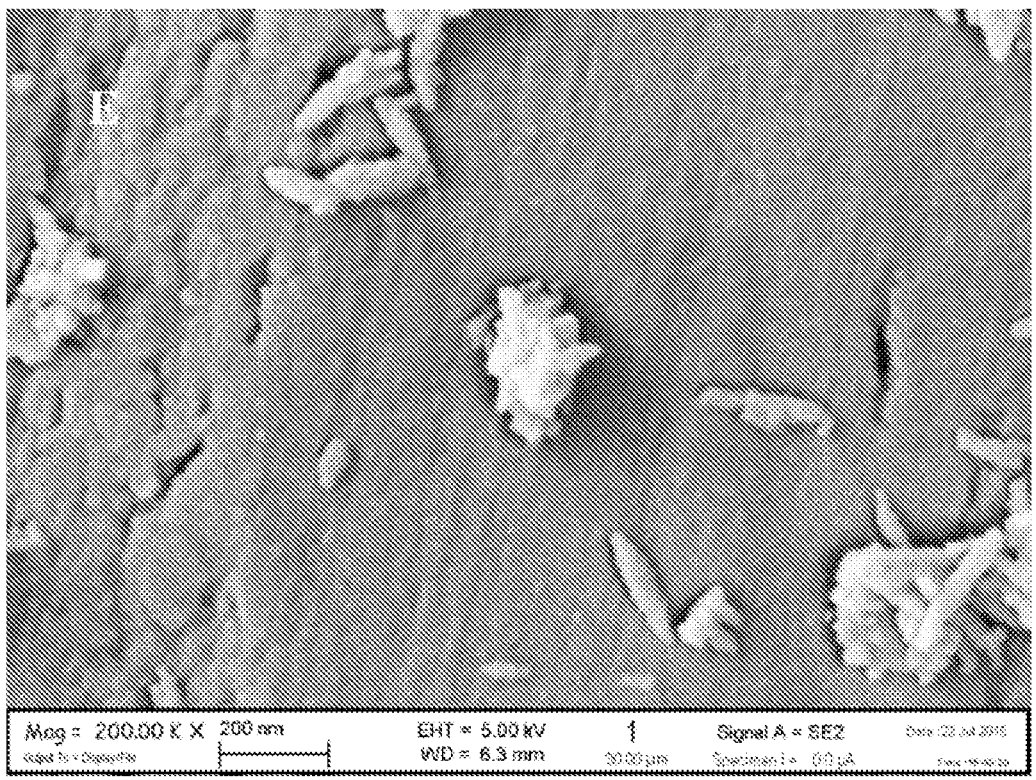
FIG. 1 shows electron microscope photomicrographs of various samples of composition of the invention.
Figure 1:
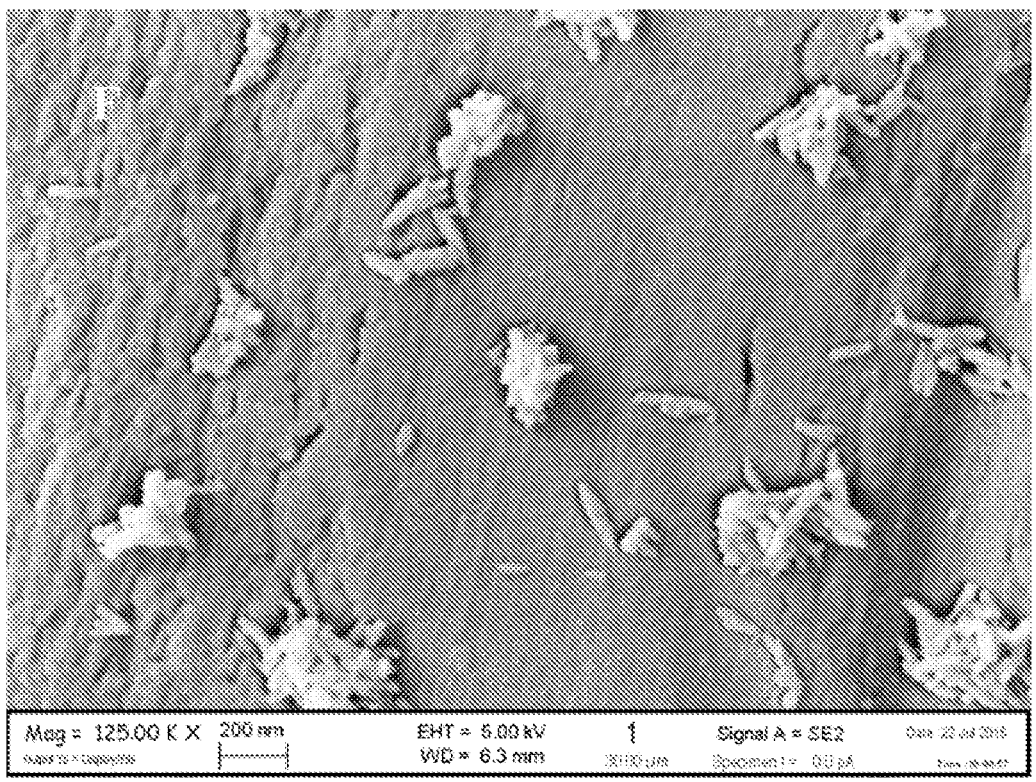

The invention is described hereinafter in detail with reference to the Figures.

Hydroxyapatite is the compound of formula $Ca_5(PO_4)_3(OH)$, often reported also as dimer $Ca_{10}(PO_4)_6(OH)_2$, which reflects the presence of two basic units in the elementary cell of the crystal. The compound naturally occurs as mineral (in which the hydroxyl ion can be partially substituted by chlorine, fluorine or carbonate ions), and is also the mineral constituent of human and animal bones. The compound is also indicated in literature by the abbreviation HA, from hydroxyapatite, which will also be used in the present text.

The inventors have verified that hydroxyapatite has such features as to allow the development of new safe solar filters, because alongside its high biocompatibility compared to ZnO and $TiO_2$, its band of absorption/reflection of the UV radiation can be extended and modulated in the desired range by introducing suitable dopant ions in its crystalline structure.

In the first aspect thereof, the invention relates to a composition comprising an organic matrix in which are present, as photoactive element, hydroxyapatite nanoparticles substituted by titanium and/or iron ions, as indicated above.

In the present invention, the term nanoparticles refers to particles whose maximum size does not exceed 500 nm; in particular, it was observed that nanoparticles obtained according to the process of the invention are generally not larger than about 200 nm.

Moreover, the matrix must of course be harmless to the surface to be protected and in the case of the skin, it must be non-toxic and ensure physiological pH values (slightly acidic pH, approximately between 4.2 and 5.6) in the finished product. The inventors have found that suitable organic matrices can be selected from polylactic acid, collagen, sodium alginate, polyethylene glycols (PEGs), chitosan, solid lipid particles (SLP) and, in particular, gelatins of known biocompatibility.

As mentioned, the photoactive component of the composition of the invention is a modified hydroxyapatite, in which an amount of between 8 and 50% atomic of phosphorus is substituted by titanium, and/or an amount of between 2 and 40% atomic of calcium is substituted by iron. The substituted HA of the invention is characterized by a reduced degree of crystallinity compared to unsubstituted HA, due to the effects of distortion of the crystalline structure induced by the presence of doping ions and to the interaction with the polymeric matrix during the process of formation of the composite material, object of the patent, which hinders the growth and maturation thereof.

The composition further contains low percentage values by weight of water, generally lower than 5%.

The HA particles contained in the composition of the invention are of nanometric size, whereby they obviate the whitening effect problem; moreover, being in close structural relation with the organic matrix and therefore part of larger composite particles, they also have a low skin penetrating power.

For the application as solar filter, after any possible addition of water, the composition of the invention is then usually mixed with other typical components of commercial products for protection against solar radiations, such as creams and oils that allow an even distribution thereof on the skin, scented oils or waterproofing components to make the cream resistant in case of immersion in water.

The second aspect of the invention relates to the process for preparing the composition described above.

The dispersion of HA nanoparticles in the matrix does not occur by mechanical mixing of previously formed HA particles in the organic matrix, but rather through a so-called "biomineralization" process, in which the HA nanoparticles are produced directly within the matrix itself.

In the biomineralization process, the organic matrix plays a fundamental role by representing the substrate on which the deposition of the inorganic phase takes place. The polymeric matrices selected for the process of the invention are rich in positive or negative charges; these charges selectively interact with cations, mainly $Ca^{2+}$, or the anions, mainly $PO_4^{3-}$, present in solution, and guide and influence the growth of the inorganic phase. In this way the polymeric matrices control the nucleation, orientation, crystallization and morphology of hydroxyapatite particles, mainly playing a role of crystallization inhibitors. As a result of this process, hydroxylapatite is nucleated on the organic matrix and in close structural relationship with it.

The process of the invention comprises the following steps:
a) preparing an aqueous solution containing a precursor of calcium and of at least one salt of iron (II) and at least one salt of iron (III);
b) preparing a hydroalcoholic solution of a titanium precursor;
c) preparing an aqueous solution, containing the constituent of the organic matrix, of a water soluble phosphorus compound;

d) adding simultaneously and slowly the solutions of the precursors of titanium and of phosphorus compound/organic matrix to the solution containing the precursor of calcium;
e) allowing the system to react at a temperature between room temperature and 70° C. for a time between 1 and 5 hours; and
f) subjecting to freeze-drying treatment the product obtained as a result of step e).

As will be apparent to the person skilled in the art, the steps mentioned above are designated by the letters a) through f) in order to identify them clearly, but this does not mean that said steps should be carried out necessarily in this sequence, and in particular steps a), b) and c) can be carried out in any sequence.

Steps a), b) and c) consist in the preparation of the solutions of the precursors of calcium/iron, titanium and phosphorus (the latter containing the constituent of the organic matrix).

For the preparation of the aqueous solution of the calcium precursor (step a), a salt thereof or preferably the hydroxide, $Ca(OH)_2$ are used. To this solution a precursor of Fe (II) and a precursor of Fe (III) are added in molar ratio of 1:1; preferred iron precursors are the nitrates thereof and, in particular, the chlorides thereof $FeCl_2.4H_2O$ and/or $FeCl_3.6H_2O$.

Preferred compounds for the preparation of the solution of titanium precursor (step b) are the chlorides and alkoxides thereof, in particular the isopropoxide (also known as isopropylate), $Ti(-O-CH(CH_3)_2)_4$; if alkoxides are used, they are preferably first dissolved in an alcohol or a hydroalcoholic mixture (the alcohol used is preferably the same whose radical is present in the compound).

The compound used for the preparation of the solution of the phosphorus precursor (step c) is a soluble phosphorus compound, which can be a salt (such as ammonium phosphate) but preferably is a phosphoric acid, and more preferably the orthophosphoric acid, $H_3PO_4$.

The hydroxyapatite formation can take place in principle by reaction of soluble salts that bring the $Ca^{2+}$ and $PO_4^{3-}$ ions in solution; in this case, salts are selected whose counterions do not interfere with the final composition, such as $Ca(NO_3)_2.4H_2O$ (nitrate as counterion of the calcium ion) and $(NH_4)_2HPO_4$ (ammonium as counterion of the phosphate ion). However, the preferred reaction is one that uses $Ca(OH)_2$ and $H_3PO_4$, since the neutralization of the acid with the base gives water as the only by-product and is particularly fast. Hereinafter, therefore, particular reference will be made to this reaction.

As mentioned, the constituent of the organic matrix that will contain the HA particles is dissolved in the solution of the phosphorus precursor. In this case, unlike calcium, phosphorus, titanium and iron, it is not a "precursor" since the organic component dissolved in solution is the same that will constitute the final matrix.

The concentrations of Ca solutions used for the synthesis reaction of substituted HA are typically in the range of 50-150 mg/mL for the Ca solution, between 75 and 110 mg/mL for P, between 12 and 100 mg/mL for titanium and between 10 and 45 mg/mL for Fe.

The amounts of Ca, Ti and Fe precursors are calculated so as to be suitable for obtaining the desired stoichiometric ratio between these three elements; if $H_3PO_4$ is used as precursor of phosphorus, this is generally added in molar amounts ranging from about 0.5 to 0.7 times with respect to the moles of the calcium precursor. The calculation of the amount of precursors of the different metals and of phosphorus depends on the particular degree of substitution of calcium desired in the final substituted hydroxyapatite and is within the skills of the average chemist.

In step d), the solutions of Ti and P precursors/organic matrix are added simultaneously to the solution containing the Ca and Fe precursors. In this step, the neutralization (salification) of the initially basic $Ca(OH)_2$ solution is carried out by the phosphoric acid; the ions present in the reaction environment interact with the molecules of the polymeric matrix and are simultaneously incorporated into the hydroxyapatite structure being formed as a result of the reaction. The resulting mixture is allowed to react for a period generally of between 1 and 5 hours, preferably under stirring at a temperature of between room T and 70° C. (step e).

With this process, the substituted HA nanoparticles are formed directly on the polymeric chains of the organic matrix. The formation within the matrix also results in obtaining nanometric dimensions; the HA nanoparticles substituted only with Ti or with Ti and Fe have spheroidal shape, or in any case homogeneous dimensions in the three spatial directions and between about 10 and 200 nm; conversely, the HA nanoparticles substituted only with Fe have a rod morphology, with a major axis having length of between about 100 and 200 nm, and minor axes having length of between about 20 and 30 nm.

The last step of the process, freeze drying, is carried out using equipment and processes that are known in the field.

The invention will be further described by the following experimental part, which includes the description of the methods for carrying out the characterization tests and examples of production of various forms of composite material of the invention and measurement of their properties.

Methods and Instrumentation

Chemical Analysis

The content of Ca, Ti, Fe, and P in the produced samples was determined using an inductively coupled plasma spectrometer (ICP-OES Liberty 200, Varian, Clayton South, Australia), which uses wavelengths of 422.673 nm (Ca), 334.941 nm (Ti), 259.940 nm (Fe) and 213.618 nm (P). The ICP analysis solutions were prepared by dissolving 20 mg of sample in a diluted $HNO_3/HCl$ solution.

The amount of $Fe^{2+}$ was measured with a colorimetric method based on the use of orthophenanthroline (1,10-phenanthroline, Merck, 99% purity), described in the article "Intrinsic magnetism and hyperthermia in bioactive Fe-doped hydroxyapatite", Tampieri A. et al., (2012) *Acta biomaterialia*, 8(2), 843-851.

Briefly, the method is based on the detection at 510 nm by UV-visible spectrophotometry (Lambda 35 UV/VIS spectrometer, Perkin Elmer) of the red-orange complex $[(C_{12}H_8N_2)_3Fe]^{2+}$ stable in the pH range of 4-5. For the measurement, 20 mg of powder are dissolved into 0.8 mL of $H_2SO_4$ (Aldrich, purity 96% by weight) after verifying that sulfuric acid does not alter the concentration of the $Fe^{2+}$ complex at least in the time necessary to perform the analysis; then, 10 mL of sodium acetate buffer (0.1 M, pH=4) are added and then, the volume of a 0.2% by weight orthophenanthroline solution is added, which is needed to obtain a nominal molar ratio $Fe^{2+}$:orthophenanthroline of 1:3. The volume of the final solution is brought to 50 mL with Millipore water. The addition of orthophenanthroline is carried out immediately after the dissolution of the sample with sulfuric acid, and the solution is analyzed 15 minutes after adding the orthophenanthroline.

The amount of $Fe^{3+}$ is determined as the difference between the total amount of Fe (determined by ICP) and the amount of $Fe^{2+}$ determined by UV-VIS with the method described above.

Diffractometric Analysis

The phase composition of each sample was determined by x-ray diffraction (XRD) using a D8 Advance diffractometer (Bruker, Karlsruhe, Germany) provided with a position-sensitive detector Lynx-eye using Cu Kα radiation ($\lambda$=1.54178 Å) generated at 40 kV and 40 mA. XRD spectra were recorded in the 2θ 10-80° range with a step (2θ) of 0.04° and a counting time of 0.5 seconds. In case of a quantitative evaluation of the phase compositions and cell parameters, a step of 0.02° was used.

SEM Analysis

The morphology of the samples was analyzed using a scanning electron microscope (SEM, FEI Quanta 200, Eindhoven, The Netherlands) and the elemental composition was assessed by energy-dispersing x-ray spectroscopy (EDX). The samples were mounted on supports made of aluminum with carbon tape. For EDX measures, an acceleration voltage of 10/12 kV and a working distance of 10 mm were used.

Thermogravimetric Analysis

The carbonate content was evaluated on dried samples by thermogravimetric analysis (TGA) using a Stanton STA 1500 instrument (Stanton, London, UK). For each test, about 10 mg of apatite were weighed in a platinum crucible and heated from room temperature to 1100° C. under nitrogen flow, with a heating rate of 10° C./min and using alumina as a reference standard. The $CO_3^{2-}$ content was evaluated based on the weight loss observed between 550 and 950° C. (a range that is relevant for the decomposition of carbonates from HA, as described in the article "The cooperative effect of size and crystallinity degree on the resorption of biomimetic hydroxyapatite for soft tissue augmentation", Iafisco, M. et al., (2010), The International journal of artificial organs, 33 (11), 765-774).

UV-Vis Absorption and Reflection

UV-Vis absorbance spectra of the samples were obtained by suspending 5 mg of powder in 5 mL of Millipore water, after which the solution was measured with a UV-VIS spectrophotometer (LAMBDA 35, Perkin Elmer). For the determination of the reflectance spectra, the spectrophotometer was provided with an integrating sphere (Labsphere RSA-PE-20). Briefly, about 50 mg of powder of the sample were introduced in a sample holder which was then placed into the slot of the integrating sphere. The equipment was calibrated with a Spectralon standard (Labsphere SRS-99-010) and the reflectance spectra were collected in the wavelength range of 280-800 nm.

Determination of Zeta Potential and Particle Size

Size and ζ potential of the samples were measured by dynamic light scattering (DLS) using a Zetasizer Nano ZS instrument (Malvern, Worcestershire, UK). The samples were suspended in water at a concentration of 0.1 mg/mL.

Small volume quartz cuvettes (105.251-QS; Hellma, Mülheim, Germany) were used to measure the size distribution. Each measurement consisted of tests of 30 seconds each, and four measurements were taken for each sample. The polydispersity index (PDI) of the samples is also calculated from the results of these measurements.

The ζ potential was determined as electrophoretic mobility by laser Doppler velocimetry using disposable electrophoretic cells (DTS1061; Malvern, Worcestershire, UK). 20 tests of 3 s each were conducted for each measurement.

Abbreviations

The following abbreviations are used in the examples below:
HA: Hydroxyapatite
Ti(iOPr)$_4$: Titanium tetraisopropylate
FeHA: Hydroxyapatite partially substituted with iron
TiHA: Hydroxyapatite partially substituted with titanium
FeTiHA: Hydroxyapatite partially substituted with iron and titanium Example 1

This example refers to the preparation of a gelatin composition biomineralized with TiHA nanoparticles.

3.32 grams of pigskin gelatin (Italgelatine) were diluted in 83 mL of Millipore water at 45° C. to obtain a 4% by weight gelatin solution. To this solution 3.46 g of phosphoric acid ($H_3PO_4$, 85% by weight aqueous solution) were added, diluted in 30 mL of Millipore water. A solution of Ti(iOPr)$_4$ was prepared separately by mixing 2.20 g of the compound with 15 mL of isopropanol (purity>99.7%). The phosphoric acid/gelatin solution and the Ti(iOPr)$_4$ solution were added dropwise to a suspension obtained by dispersing 3.90 g of Ca(OH)$_2$ (97% purity) in 100 mL of Millipore water at 45° C.

The resulting mixture was allowed to react under stirring for 2 hours at 45° C., and then at rest at room temperature for 2 more hours. The resulting solid fraction was removed by centrifugation and repeatedly washed with water. In the end, the sample thus obtained was brought to −40° C. and freeze-dried. This sample was named Gel-TiHA. The SEM photomicrographs identified as C and D in FIG. 1 show, at two different magnifications, the particles of this sample; as can be seen in the images, the Gel-TiHA sample consists of particles with similar dimensions in the three spatial directions, of between about 100 and 200 nm.

Example 2

This example refers to the preparation of a gelatin composition biomineralized with FeHA nanoparticles.

A process similar to that in example 1 was followed for the mineralization of gelatin with FeHA. Briefly, 4.2 g of phosphoric acid were mixed with 100 mL of a 4% by weight solution of pigskin gelatin. Two solutions of iron salts were prepared separately by adding 1.25 g of FeCl$_2$.4H$_2$O (purity>99.0%) and 1.74 g of FeCl$_3$.6H$_2$O (purity>99.0%) to 8 mL of Millipore water for each, respectively. Finally, a suspension of calcium precursor was prepared by mixing 4.72 g of Ca(OH)$_2$ with 100 mL of Millipore water at 45° C. The two solutions of iron salts were poured simultaneously in the suspension of Ca(OH)$_2$ and the solution of phosphoric acid/gelatin was added dropwise immediately afterwards. At the end of the neutralization reaction, the resulting solid sample was recovered by centrifugation, repeatedly washed with water, brought to −40° C. and freeze-dried. This sample was named Gel-FeHA. The SEM photomicrographs identified as E and F in FIG. 1 show, at two different magnifications, the particles of this sample; as can be seen in the images, the Gel-FeHA sample consists of particles with needle-like morphology, with a major axis having length of between about 100 and 200 nm and minor axes having length of between about 20 and 30 nm.

Example 3

This example refers to the preparation of a gelatin composition biomineralized with FeTiHA nanoparticles.

For the mineralization of gelatin with FeTiHA, the two procedures described for obtaining Gel-TiHA and Gel-FeHA were combined. Briefly, 4.2 g of phosphoric acid were mixed with 30 mL of Millipore water and then with 125 mL of a 4% by weight solution of pigskin gelatin. The titanium precursor solution was obtained by mixing 3.15 g of Ti(iOPr)$_4$ with 15 mL of isopropanol. The calcium precursor suspension was prepared by adding 4.72 g of Ca(OH)$_2$ to 100 mL of Millipore water at 45° C. Two solutions of iron precursors were prepared by dissolving 1.2 g of FeCl$_2$.4H$_2$O and 1.65 g of FeCl$_6$.6H$_2$O into 8 mL of Millipore water for each, respectively. The two iron precursor solutions were poured into the calcium precursor solution, and the two solutions of phosphoric acid/gelatin and Ti(iOPr)$_4$ were added dropwise to the mixture thus obtained immediately afterwards. At the end of the neutralization reaction, the resulting solid sample was recovered by centrifugation, repeatedly washed with water, brought to −40° C. and freeze-dried. This sample was named Gel-FeTiHA. The SEM photomicrographs identified as A and B in FIG. 1 show, at two different magnifications, the particles of this sample; as can be seen in the images, the Gel-FeTiHA sample consists of particles with morphology and dimensions similar to those of the Gel-TiHA sample.

Example 4

Thermogravimetric and ICP analyses were conducted on the samples prepared in Examples 1-3 to determine the chemical composition thereof.

Thermogravimetric analyses determine the composition of the samples in terms of % by weight of water, gelatin and mineral fraction. The water and gelatin contents were calculated by the weight losses that occur in the range 25-110° C. and 120-1000° C., respectively, attributing the residual mass to the substituted HA. The results of these analyses are shown in Table 1.

TABLE 1

| Component | Gel-TiHA (% by weight of components) | Gel-FeHA (% by weight of components) | Gel-FeTiHA (% by weight of components) |
|---|---|---|---|
| HA | 73.61 | 81.68 | 77.52 |
| Gelatin | 20.93 | 13.82 | 17.21 |
| Water | 2.16 | 2.26 | 2.50 |

The values of water amounts were very similar in the three samples; the amounts of gelatin and HA instead showed greater variations in the different samples.

The chemical composition of the mineral part (substituted HA) was measured with the ICP quantitative analysis in terms of atomic ratios between the various elements; the test results are summarized in Table 2.

In general, all the samples show a very different Ca/P atomic ratio value from pure HA (theoretical ratio 1.67): the values of this ratio are lower than the theoretical and similar in the Gel-FeHA and Gel-FeTiHA samples (1.33 and 1.35, respectively), while that of the Gel-TiHA sample, 1.90, is significantly higher than the theoretical.

The Ti/Ca atomic ratio of the Gel-TiHA sample is in accordance with the amount of titanium nominally introduced during its preparation, while the atomic Ca/(P+Ti) ratio deviates from the Ca/P ratio of stoichiometric HA.

In the Gel-FeTiHA sample, the Ti/Ca atomic ratio (0.21) is greater than that of the Gel-TiHA sample and even higher than that derivable from the nominal amount of titanium introduced during synthesis (15 mol % with respect to Ca). Moreover, a very low atomic Ca/(P+Ti) ratio was measured in this sample, equal to 1.05; this can be attributed to the substitution of Ca with Fe ions, as confirmed by the atomic ratio (Ca+Fe)/P of 1.63, a value close to that of stoichiometric HA. These data suggest the presence of a secondary phase of TiO$_2$.

Finally, the Gel-FeHA sample shows a greater relative content of Fe with respect to Gel-FeTiHA: the Fe/Ca atomic ratio in the two samples is 0.33 and 0.21, respectively. As a result, also the values of the atomic ratio (Ca+Fe)/P are higher in Gel-FeHA (1.77) than in Gel-FeTiHA (1.63). The Fe$^{2+}$/Fe$^{3+}$ ratio for both samples is instead in complete accordance with the amounts of the two ions nominally introduced during synthesis.

Example 5

Figure 2:
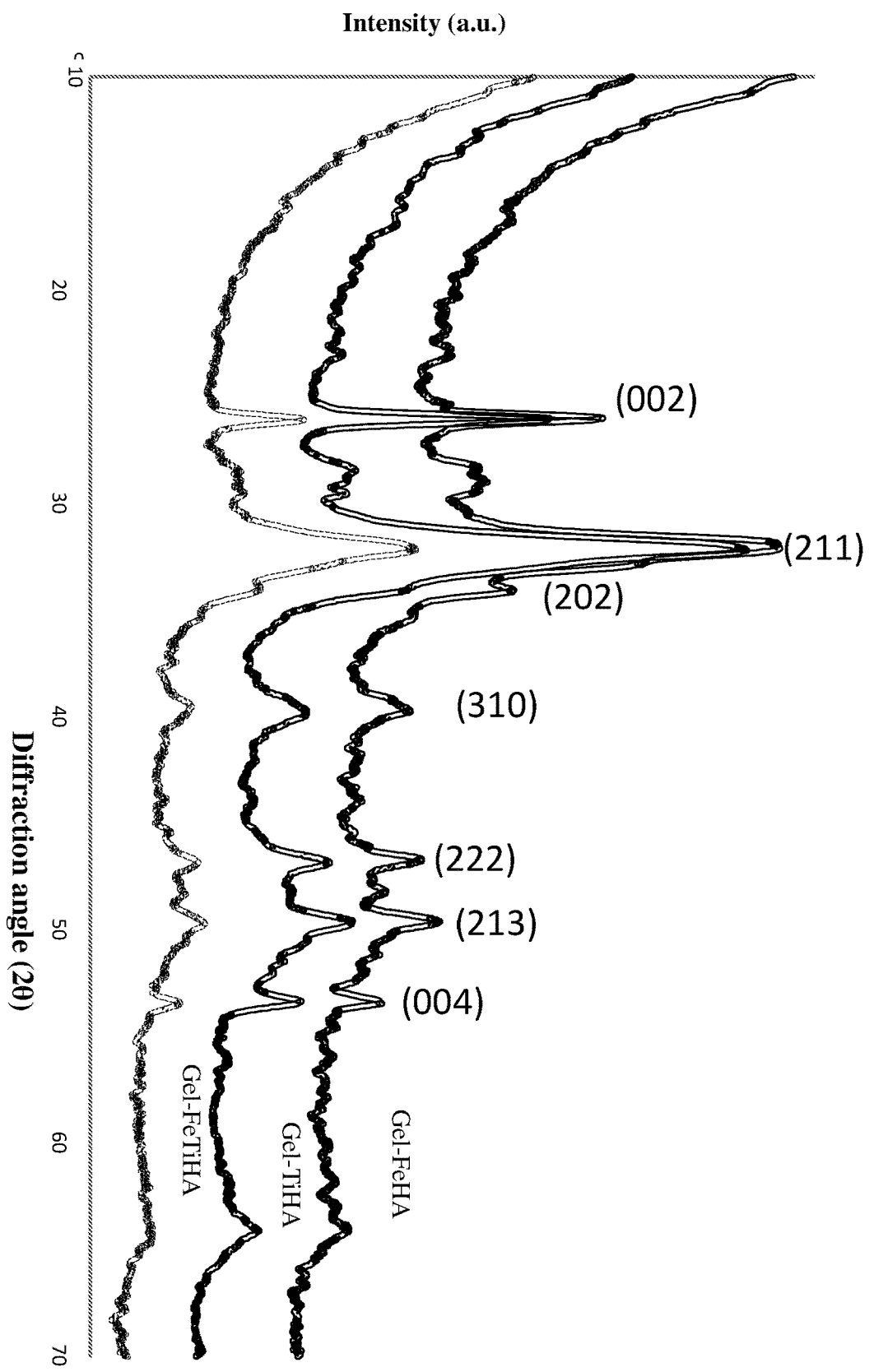
FIG. 2 shows the powder x-ray diffraction spectrum of three samples of composition of the invention.

Powder x-ray diffraction analyses (XRD) were conducted on the three samples prepared in Examples 1-3. All three spectra are shown in FIG. 2, mutually staggered along the vertical axis to distinguish them: the spectrum relating to the Gel-FeTiHA sample is the lower one in the figure, the one relating to Gel-TiHA is the middle one and that relating to Gel-FeHA is in the upper part of the figure.

The XRD profiles show, for all three samples, only the presence of a crystalline phase that can be identified as HA: the peak positions correspond to literature data attributable (through Miller indexes, shown in the figure) to this compound. No secondary crystalline phase is identified; on the basis of this observation, it can be concluded that the TiO$_2$ phase, whose presence is inferred from the chemical analyses of example 4, is amorphous. Of course, diffraction peaks attributable to the gelatin were not detected, since this is an amorphous organic polymer.

All the peaks of the three diffractograms are poorly resolved, with low relative intensity with respect to the background and a low ratio of height to width at half height, especially in the case of Gel-FeTiHA. These characteristics of the peaks are an indication of low degree of crystallinity of the material. This may be ascribed to various factors. Firstly, the low biomineralization temperature does not allow an atomic rearrangement in favor of more crystalline structures, which are thermodynamically more stable. A

TABLE 2

| | Ca/P | Fe/Ca | Ti/Ca | (Ca + Fe)/P | Ca/(P + Ti) | Fe$^{2+}$/Fe$^{3+}$ |
|---|---|---|---|---|---|---|
| Gel-TiHA | 1.90 ± 0.2 | / | 0.15 ± 0.03 | / | 1.48 ± 0.10 | / |
| Gel-FeHA | 1.33 ± 0.1 | 0.33 ± 0.08 | / | 1.77 ± 0.13 | / | 1:1 |
| Gel-FeTiHA | 1.35 ± 0.1 | 0.21 ± 0.05 | 0.21 ± 0.05 | 1.63 ± 0.05 | 1.05 | 1:1 | second factor is the presence of the gelatin: amorphous organic polymers can direct the mineralization process towards low crystallinity phases, as is known in the field. Finally, the presence of iron and/or titanium ions during biomineralization, in which the crystal lattice is formed, has the effect of distorting the lattice itself, thus leading to an increase in disorderly areas and causing the formation of poorly crystalline HA.

Example 6

Hydrodynamic diameter (Hd) values, polydispersity index (PDI) and potential of the samples prepared in Examples 1-3 were measured using the instruments and methods described above.

The results are shown in Table 3.

TABLE 3

| Sample | Hd (nm) | PDI | ζ potential (mV) |
|---|---|---|---|
| Gel-TiHA | 531.3 ± 7.9 | 0.17 ± 0.05 | 3.12 ± 0.2 |
| Gel-FeHA | 552.0 ± 34.7 | 0.47 ± 0.03 | −15.1 ± 1.4 |
| Gel-FeTiHA | 421.9 ± 19.4 | 0.10 ± 0.06 | −10.4 ± 0.7 |

Hd values recorded by light diffraction are much higher than those measured by SEM analysis; these values are hundreds of nanometers for each sample, with similar values for Gel-TiHA and Gel-FeHA (531.3 nm and 552.0 nm, respectively), and only slightly lower for Gel-FeTiHA (421.9 nm). This difference is due to the fact that for SEM analysis, the samples were suspended in ethanol and dried by means of an infrared lamp on alumina matrix, while for the DLS analysis it was necessary to prepare a suspension. In this way, while with the SEM it was possible to determine the size of the single dry particles, the result obtained with the DLS analysis determines the size of the particles in the aqueous medium, providing additional information on the behavior of the gelatin particles mineralized in water. As is well known in literature, nano-sized particles tend to clump together when they are suspended in aqueous media, so that the values obtained from DLS do not relate to single particles but to aggregates thereof.

Example 7

Figure 3:
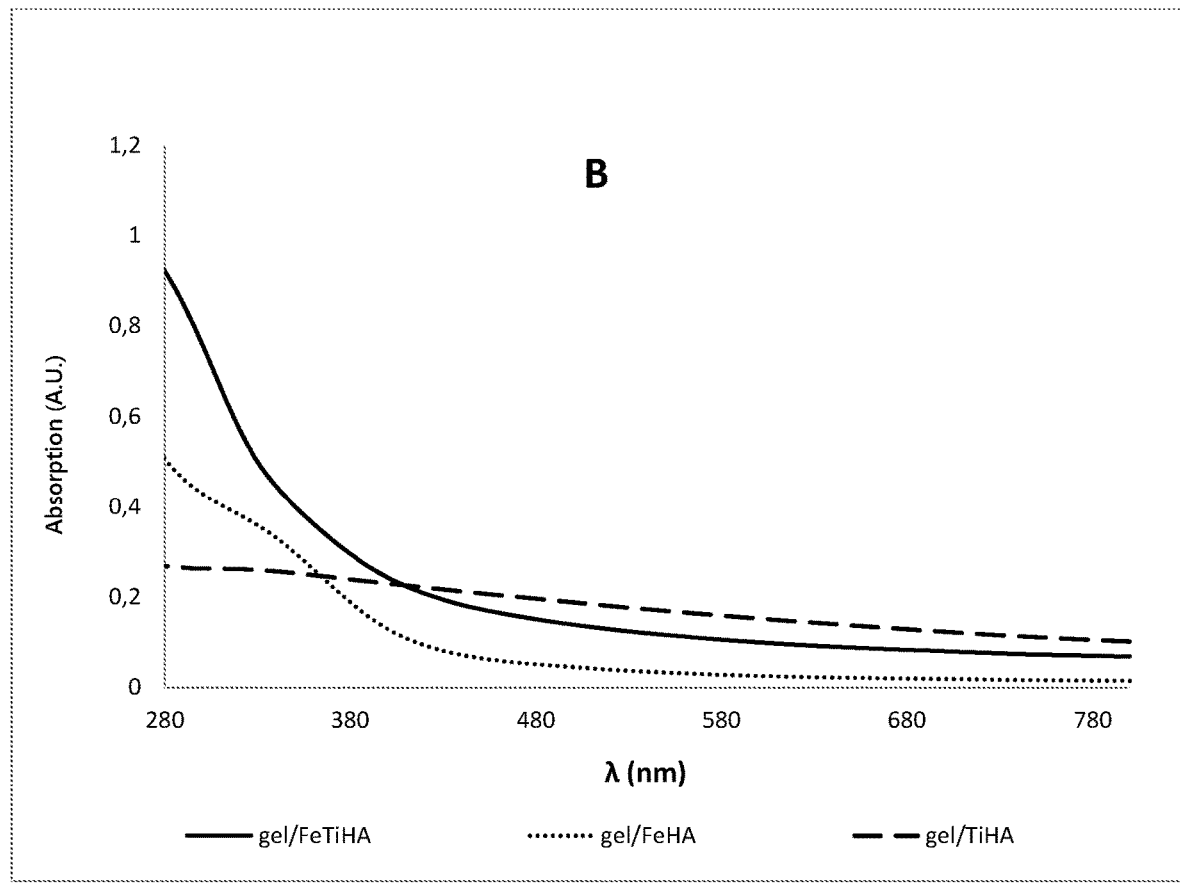
FIGS. 3.A and 3.B show the reflectance and absorption spectra, respectively, of UV-visible light by samples of composition of the invention.

The UV-Vis light absorption and reflection properties of the composition of the invention were measured using the instruments and methods described above. The results are shown in FIG. 3. FIG. 3.A shows the reflectance spectra of the samples, in terms of percentage of reflected radiation as a function of the wavelength; absorbance spectra are shown in FIG. 3.B, in arbitrary units (a. u.), as a function of the wavelength.

The reflectance profiles of Gel-FeHA and Gel-FeTiHA are similar to each other, with a relatively low reflectance capacity (about 20%) at wavelengths in the range of 280-500 nm, followed by a gradual increase up to reach 60% of the light reflected around 650 nm wavelength. On the other hand, the reflectance profile of Gel-TiHA is very different, with an area of average reflectance between 280 and 320 nm, followed by a rapid increase up to reach the maximum reflectance (90%) at about 350 nm; after this peak, the reflectance decreases slowly but never drops below values of about 65% (at 800 nm).

As regards the behavior in absorption as well, Gel-FeHA and Gel-FeTiHA have similar profiles, with maximum values recorded at 280 nm, followed by an inflection point at about 360 nm and then rapid decrease up to about 400 nm, after which the absorption value remains essentially constant throughout the visible field. On the other hand, the Gel-TiHA sample, across the entire measuring range, shows low levels of absorption, with a profile that decreases in an almost linear manner with increasing wavelength.

These results demonstrate that Gel-TiHA has excellent reflectance properties in the UVA range (maximum reflectance at 350 nm) and can reflect the radiation also in the UVB range (reflectance values never lower than 65%). Gel-FeHA and Gel-FeTiHA instead have good absorption properties in the UVB range. These properties make Gel-TiHA a physical filter, efficient for a sunscreen composition, while Gel-FeHA and Gel-FeTiHA can be used in combination with the first one to extend and increase the range of protection and the protective efficacy of solar filters in the UVB range.

The invention claimed is:

1. Composition for the preparation of physical solar filters, comprising an organic matrix formed by polymer molecules, onto which are nucleated nanoparticles of hydroxyapatite substituted with titanium, in which phosphorus is partially replaced by titanium in an amount between 8 and 50% atomic with respect to phosphorus, and in which calcium is optionally partially replaced by iron in an amount between 2 and 40% atomic with respect to calcium, and wherein the composition comprises between 5 and 60% by weight of the organic matrix, between 35 and 90% by weight of the substituted hydroxyapatite, and water.

2. The composition according to claim 1, wherein the organic matrix is selected from polylactic acid, collagen, sodium alginate, polyethylene glycols (PEGs), chitosan, solid lipid particles (SLPs) and gelatins.

3. The composition according to claim 1 wherein said hydroxyapatite particles have a size between 10 and 200 nm.

* * * * *